US008039482B2

(12) United States Patent  
Sugihara et al.

(10) Patent No.: US 8,039,482 B2
(45) Date of Patent: Oct. 18, 2011

(54) COMPOSITION OF SOLIFENACIN OR SALT THEREOF FOR USE IN SOLID FORMULATION

(75) Inventors: Akio Sugihara, Yaizu (JP); Takehiko Yasuji, Yaizu (JP); Katsuhiro Masaki, Yaizu (JP); Daisuke Murayama, Yaizu (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/594,127

(22) PCT Filed: Mar. 24, 2005

(86) PCT No.: PCT/JP2005/005377
§ 371 (c)(1),
(2), (4) Date: Sep. 25, 2006

(87) PCT Pub. No.: WO2005/092889
PCT Pub. Date: Oct. 6, 2005

(65) Prior Publication Data
US 2008/0039516 A1 Feb. 14, 2008

Related U.S. Application Data

(60) Provisional application No. 60/556,025, filed on Mar. 25, 2004, provisional application No. 60/638,388, filed on Dec. 27, 2004.

(51) Int. Cl.
*C07D 453/02* (2006.01)
*C07D 453/04* (2006.01)
*A01N 43/90* (2006.01)
(52) U.S. Cl. .................. 514/305; 546/135
(58) Field of Classification Search .................. 546/135; 514/305
See application file for complete search history.

(56) References Cited

U.S. PATENT DOCUMENTS

| 4,870,059 | A | 9/1989 | Mitsuhashi et al. |
| 5,075,114 | A | 12/1991 | Roche |
| 5,082,669 | A | 1/1992 | Shirai et al. |
| 5,260,072 | A | 11/1993 | Roche et al. |
| 5,534,534 | A | 7/1996 | Makino et al. |
| 5,607,697 | A | 3/1997 | Alkire et al. |
| 5,997,903 | A | 12/1999 | Dietrich et al. |
| 6,011,062 | A | 1/2000 | Schneider |
| 6,017,927 | A | 1/2000 | Takeuchi et al. |
| 6,221,402 | B1 | 4/2001 | Itoh et al. |
| 2002/0119196 | A1 | 8/2002 | Parikh et al. |
| 2002/0155156 | A1 | 10/2002 | Mulye |
| 2003/0096791 | A1 | 5/2003 | Gupte et al. |
| 2004/0136915 | A1 | 7/2004 | Dugger, III et al. |
| 2004/0138253 | A1* | 7/2004 | Slatter ............... 514/305 |
| 2004/0198822 | A1* | 10/2004 | Fraser et al. ........... 514/561 |
| 2005/0175689 | A1 | 8/2005 | Kurimoto et al. |
| 2005/0181031 | A1* | 8/2005 | Saito et al. ............ 424/448 |
| 2005/0239890 | A1* | 10/2005 | Fraser et al. ........... 514/561 |
| 2006/0035923 | A1 | 2/2006 | Van Meeteren et al. |
| 2006/0147531 | A1 | 7/2006 | Segula et al. |
| 2007/0231399 | A1 | 10/2007 | Kasashima et al. |
| 2007/0270459 | A1 | 11/2007 | Van Meeteren et al. |
| 2008/0103171 | A1* | 5/2008 | Umejima et al. ........... 514/305 |

FOREIGN PATENT DOCUMENTS

| CN | 1171109 A | 1/1998 |
| EP | 0121291 A2 | 10/1984 |
| EP | 0 459 695 A1 | 12/1991 |
| EP | 0459695 A1 | 12/1991 |
| EP | 0 473 431 A1 | 3/1992 |
| EP | 0473431 A1 | 3/1992 |
| EP | 0801067 A1 | 10/1997 |
| EP | 1219291 A1 | 7/2002 |
| EP | 1552825 A1 | 7/2005 |
| EP | 1 714 965 A1 | 10/2006 |
| EP | 1 726 304 A1 | 11/2006 |
| EP | 1728791 A1 | 12/2006 |
| EP | 1832288 A1 | 9/2007 |
| JP | 62-136240 A | 6/1987 |
| JP | 5-194218 A | 8/1993 |
| JP | 06-219939 A | 8/1994 |
| JP | 06-316536 A | 11/1994 |
| JP | 9-71764 A | 3/1997 |
| JP | 9-110698 A | 4/1997 |
| JP | 10-7547 A | 1/1998 |
| JP | 2000-514830 A | 11/2000 |
| JP | 2002-272817 A | 9/2002 |
| JP | 2003-261439 A | 9/2003 |

(Continued)

OTHER PUBLICATIONS

Yasushi et al., "Effects of Compression Pressure on Physical and Chemical Stability of Tablets Containing an Anticancer Drug TAT-59[1-3]" (1994), Chem. Pharm. Bull., vol. 42, No. 12, pp. 2582-2587.
Owen C. Chidavaenzi et al., "The effect of co-spray drying with polyethylene glycol 4000 on the crystallinity and physical form of lactose" (2001), International Journal of Pharmaceutics, vol. 216, pp. 43-49.
Ching-Wei et al., "Effect of particle size on the available surface area of nifedipine from nifedipine-polyethylene glycol 6000 solid dispersions" (1996), International Journal of Pharmaceutics, vol. 127, pp. 261-272.
Deirdre O. Corrigan et al., "The effect of spray drying solutions of bendroflumethiazide/polyethylene glycol. on the physicochemical properties of the resultant materials" (2003), International Journal of Pharmaceutics, vol. 262, pp. 125-137.

(Continued)

*Primary Examiner* — D M Seaman
*Assistant Examiner* — Niloofar Rahmani
(74) *Attorney, Agent, or Firm* — Sughrue Mion, PLLC

(57) ABSTRACT

A solid pharmaceutical preparation of solifenacin or a salt thereof, the preparation being stable and inhibited from decomposing with time when supplied to clinical fields. In a pharmaceutical preparation containing solifenacin or a salt thereof, the compound in an amorphous form was revealed to be causative of cardinal-drug decomposition with time. The composition for a solid pharmaceutical preparation of solifenacin or a salt thereof contains solifenacin or its salt each in a crystalline from, and the content provided are: a process for producing the composition; and a medicinal composition for solid pharmaceutical preparations which contains solifenacin and an amorphization inhibitor.

3 Claims, No Drawings

FOREIGN PATENT DOCUMENTS

| | | |
|---|---|---|
| JP | 2004026675 A | 1/2004 |
| JP | 2004-175796 A | 6/2004 |
| RU | 2 090 567 C1 | 9/1997 |
| RU | 2 136 685 C1 | 9/1999 |
| WO | WO 96/20194 A1 | 7/1996 |
| WO | 98/30209 A1 | 7/1998 |
| WO | 02/096392 A1 | 12/2002 |
| WO | 03/006019 A1 | 1/2003 |
| WO | 03/099268 A1 | 12/2003 |
| WO | WO 03/103659 A1 | 12/2003 |
| WO | 2005-039542 A1 | 5/2005 |
| WO | 2005-092889 A1 | 10/2005 |
| WO | 2006/070735 A1 | 7/2006 |

OTHER PUBLICATIONS

Claes Ahlneck et al., "The molecular basis of moisture effects on the physical and chemical stability of drugs in the solid state" (1990), International Journal of Pharmaceutics, vol. 62, pp. 87-95.
Russian Office Action dated Mar. 24, 2008.
Mealy N., et al., "Treatment of Urinary Incontinence Muscarinic M3 Antagonist", Drugs of the Future, Prous Science, vol. 24, No. 8, Jan. 1, 1999, pp. 871-874, XP001061585.
Hedge Sharath S., "Antimuscarinics for the treatment of overactive bladder: Current options and emerging therapies", Current Opinion in Investigational Drugs, vol. 5, No. 1, Jan. 1, 2004, pp. 40-49, XP008061336.
"VESIcare", www.rxlist.com/vesicare-drug.htm, p. 1, XP002500528.
"Amorphous Solids: Implications for Solubility and Stability", www.ssci-inc.com/Information/RecentPublications/ApplicationNotes/AmorphousSolidsImplications/tabid/142/Default.aspx, 2003, pp. 1-3, XP0025005273.
Supplementary European Search Report dated Nov. 10, 2008.
Chinese Office Action, dated May 8, 2009.
European Office Action dated Jun. 22, 2009.
Non-Final Office Action issued Nov. 1, 2007 in U.S. Appl. No. 11/458,582.
Non-Final Office Action issued Jun. 26, 2008, in U.S. Appl. No. 11/458,582.
Final Office Action issued Jan. 30, 2009, in U.S. Appl. No. 11/458,582.
Non-Final Office Action issued Jul. 17, 2009, in U.S. Appl. No. 11/458,582.
Non-Final Office Action issued Dec. 27, 2007 in U.S. Appl. No. 10/975,210.
Final Office Action issued Sep. 11, 2008 in U.S. Appl. No. 10/975,210.
Non-Final Office Action issued May 27, 2009 in U.S. Appl. No. 10/975,210.
Non-Final Office Action issued Jun. 11, 2009 in U.S. Appl. No. 11/721,863.
IPRP (PCT/ISA/237) dated Feb. 21, 2006 filed in U.S. Appl. No. 11/721,863.
Office Action (Interview Summary) issued in U.S. Appl. No. 11/458,582 dated Oct. 31, 2008.
Office Action issued in counterpart Russian Patent Application No. 2007128815/15(031373) dated Nov. 2, 2009.
Extended European Search Report dated Jan. 25, 2010 in European Application No. 05820232.6.
Extended European Search Report dated Jan. 25, 2010 in European Application No. 09014500.4.
Mexican Office Action dated Mar. 19, 2010 in Mexican Application No. MX/E/2009/075271.
Japanese Office Action dated Jan. 5, 2010, in Japanese Application No. 2006-511,497.
Australian Office Action dated Apr. 23, 2010 in Australian Application No. 2005226357.
Indonesian Office Action dated May 18, 2010, in Indonesian Application No. W-00 2006 02634.
Chinese Office Action dated Nov. 11, 2009 in Chinese Application No. 2005800450144.
Japanese Office Action dated Nov. 19, 2009 in Japanese Application No. 2006-550,756.
U. S. Office Action dated Feb. 2, 2010 in U.S. Appl. No. 10/975,210.
Office Action issued on Mar. 17, 2010 in Australian Application No. 2005320672.
Office Action issued on May 4, 2010 in Indonesian Application No. W-00 2007 02057.
Philippine Office Action issued Jun. 23, 2010 in corresponding Philippine Application No. 1-2006-501883.
Korean Office Action issued Jun. 16, 2010 in corresponding Korean Application No. 10-2006-7019783.
Third Party Observation issued Apr. 13, 2010 in corresponding European Application No. 05721391.0.
L. Yu, "Amorphous pharmaceutical solids: preparation, characterization and stabilization," Advanced Drug Delivery Reviews, vol. 48, pp. 27-42 (2001).
B. Hancock, "Characteristics and Significance of the Amorphous State in Pharmaceutical Systems," Journal of Pharmaceutical Sciences, vol. 86, No. 1, pp. 1-12 (1997).
Solifenacin Succinate: Crystallization experiments.
E. Shalaev et al., "How Does Residual Water Affect the Solid-State Degradation of Drugs in the Amorphous State," Journal of Pharmaceutical Sciences, vol. 85, No. 11, pp. 1137-1141 (1996).
International Search Report (ISA) issued Jan. 25, 2005 in PCT/JP2004/016196.
International Preliminary Report on Patentability (IPRP) issued in PCT/JP2004/016196.
International Search Report (ISA) issued Sep. 12, 2006 in PCT/JP2006/314250.
International Preliminary Report on Patentability (IPRP) issued Jan. 22, 2008 in PCT/JP2006/314250.
European Third Party Observation issued Jul. 27, 2010 in European application No. 05721391.0.
X1, Yamanouchi, VESICARE, Module 13.nl.PI, Section 1.3: Product Information (2003).
X2, Yamanouchi, VESICARE, Register, RVG 29151, College Ter Beoordeling Van Geneesmiddelen, Medicine Evaluation Board (2003).
X3, Yamanouchi, VESICARE, Register, RVG 29152, College Ter Beoordeling Van Geneesmiddelen, Medicine Evaluation Board (2003).
International Preliminary Report on Patentability (IPRP) issued Oct. 19, 2006 in PCT/JP2005/005377.
Chinese Office Action issued Jul. 12, 2010, in the corresponding Chinese Patent Application No. 200910159953.1.
Israeli Office Action issued on Aug. 10, 2010, in corresponding Israeli Patent Application No. 178249.
Ansel, Howard C. et., al. "Pharmaceutical Dosage Forms and Drug Delivery Systems", Seventh Edition, 1999, pp. 39, 87-92, 109, 110, 232 and 233.
U.S. Office Action issued on Sep. 16, 2010 in the co-pending U.S. Appl. No. 11/721,863.
Philippines Office Action, dated Dec. 1, 2010, issued in Application No. 12007501197.
Canadian Office Action, dated Aug. 23, 2010, issued in Application No. 2,561,167.
Chinese Office Action dated Nov. 18, 2010, issued in Application No. 200580045014.4.
Korean Office Action, dated Dec. 30, 2010, issued in Application No. 10-2006-7019783.
Chinese Office Action, dated Feb. 9, 2011, issued in Application No. 200910159953.1.
Israeli Office Action, dated Feb. 20, 2011, issued in Application No. 167046.
Japanese Office Action, dated Mar. 11, 2011, issued in Application No. 2006-511497.
Christine Heading, "Current Opinion in Central & Peripheral Nervous System Investigational Drugs", vol. 2, No. 3, 2000, pp. 321-325.
US Advisory Action, dated Dec. 29, 2010, issued in co-pending U.S. Appl. No. 11/721,863.

Korean Office Action dated Apr. 12, 2011 issued in Korean Patent Application No. 10-2011-7007484.

Office Action issued on Apr. 28, 2011 by the State of Isreal in the corresponding Israeli Patent Application No. 183877.

European Office Action issued Jul. 18, 2011, in corresponding Application No. 05820232.6.

European Office Action dated Jul. 27, 2011, in application No. 05721391.0.

European Communication, dated Aug. 3, 2011, issued in Application No. 09014500.4.

* cited by examiner

COMPOSITION OF SOLIFENACIN OR SALT THEREOF FOR USE IN SOLID FORMULATION

This is a 371 national stage based on PCT/JP2005/005377 filed Mar. 24, 2005, and claims benefit and priority from U.S. Provisional Application 60/556,025 filed Mar. 25, 2004 and U.S. Provisional Application 60/638,388 filed Dec. 27, 2004. Each of the referenced PCT and U.S. Provisional Applications is incorporated herein by reference.

TECHNICAL FIELD

The present invention relates to a composition of solifenacin or a salt thereof for use in solid formulation, the composition containing the crystal of solifenacin or a salt thereof at an amorphous content within a range with no influence on the stability of the resulting product, as well as a method for producing the same. Additionally, the invention relates to a pharmaceutical composition containing solifenacin or a salt thereof and an inhibitor of amorphous preparation.

BACKGROUND ART

Solifenacin is represented by the following formula (I):

[Chemical formula 1]

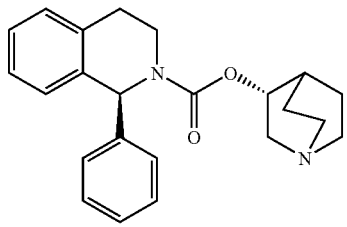

Formula (I)

and is chemically called (1R,3'R)-3'-quinuclidinyl 1-phenyl-1,2,3,4-tetrahydro-2-isoquinoline carboxylate.

It is reported that a series of quinuclidine derivatives including solifenacin or salts thereof have an excellent selective antagonistic action against muscarine $M_3$ receptors and are useful as prophylactic or therapeutic agents of urinary diseases such as nervous pollakiuria, neurogenic bladder, nocturnal enuresis, unstable bladder, bladder contracture, and chronic cystitis as well as respiratory diseases such as chronic occlusive lung diseases, chronic bronchitis, asthma and rhinitis (see patent reference 1).

A manufacturing process of solifenacin hydrochloride is described in Example 8 in the patent reference 1, wherein the crystal resulting from crystallization in a mixture solvent of acetonitrile and diethyl ether has a melting point of 212 to 214° C. and has a specific rotation ($[\alpha]^{25}_D$ of 98.1 (c=1.00, EtOH).

However, the patent reference 1 includes no description or suggestion about significant degradation over time of amorphous solifenacin or an amorphous salt thereof or solifenacin succinate as an active pharmaceutical ingredient in a formulation when solifenacin succinate product is formulated by a general pharmaceutical manufacturing process.

Non-patent reference 1 publicly issued by the Japanese Ministry of Health, Labor and Welfare in June, 2003 includes the description about the specification of drug products, namely the concept about degradation products (impurities) in new drug products as observed at stability tests. According to the reference, the threshold of a degradation products requiring safety qualification in a drug product is a lower one of either 1.0% as the percentage of the degradation product contained in a drug substance or 50 µg as the total daily intake of the degradation product, when the amount of the drug substance to be administered per day is less than 10 mg. When the amount of the drug substance to be administered per day is 10 mg or more to 100 mg or less, the threshold of a degradation product requiring safety qualification in a drug products is a lower one of either 0.5% as the percentage of the degradation product contained in a drug substance or 200 µg as the total daily intake of the degradation product. Therefore, the specification of a degradation product as can be determined with no requirement of any safety qualification of the degradation product is generally 1.0% or less as the percentage of the degradation product contained in a drug substance, when the formulation is for example at a 5-mg content of the drug substance. When the formulation is for example at a 10-mg content of the drug substance, the percentage of the degradation product contained in the drug substance is 0.5% or less.

Solifenacin formulations, currently planned in a market on the basis of clinical test results, are 2.5-mg, 5-mg, and 10-mg tablets. For these formulations to have the stability described in the non-patent reference 1, it was considered that the amount of the main degradation product (abbreviated as F1 hereinafter) of solifenacin succinate to the total amount of solifenacin succinate and degradation products thereof should be set at 0.5% or less and that the amount should be controlled to 0.4% or less, considering lot-to-lot variation and test errors.

Patent reference 1: Specification of EP 801 067
Non-patent reference 1: Notification No. 0624001 issued by Japanese Committee of Pharmaceutical Affairs, "Revision of Guideline about Impurities in New Drug Products containing Novel Active Pharmaceutical Ingredients"

DISCLOSURE OF THE INVENTION

Problems that the Invention is to Solve

The present inventors granulated solifenacin succinate by the fluidized bed granulation process under general conditions for persons skilled in the art and manufactured the tablets for developing solifenacin succinate as an excellent therapeutic agent of pollakiuria and incontinence of urine. Then, the inventors carried out a preliminary stability test of the resulting tablet over 6 months at an acceleration test (at 40° C. and 75% RH (relative humidity) using bottle-sealing conditions) as one of general stability tests. Consequently, the inventors observed the decrease in the residual ratio of solifenacin succinate, so that the amount of the generated F1 to the total amount of solifenacin succinate and degradation products thereof exceeded 0.4% (see Table 2 below in detail) The inventors understood that it was difficult to obtain a formulation thereof with pharmaceutically sufficient stability by such general pharmaceutical manufacturing process.

In providing a solid formulation of solifenacin or a salt thereof as an excellent therapeutic agent of pollakiuria and incontinence of urine, in other words, the development of a solid formulation of solifenacin or a salt thereof stable over time has been desired strongly, which can inhibit the amount of F1 generated to the total amount of solifenacin or a salt thereof and degradation products thereof to 0.4% or less.

Means for Solving the Problems

The degradation of a drug substance in a formulation generally involves for example redox reaction, hydrolysis reaction, racemization, photodegradation and polymeric degradation. It has been described that these reactions have a correlation with heat, oxygen, light, water and interactions with other components. As described above, numerous causes in relation with drug degradation should be considered so as to obtain stable drug products. In such state of technical level, the inventors made investigations about the stabilization of solifenacin products. Unexpectedly, the inventors elucidated that amorphous solifenacin succinate generated during a manufacturing process of the drug products was the main cause of the degradation of the active pharmaceutical ingredient over time.

Additionally, the inventors found that the amorphous content in the drug products could be inhibited by adjusting the moisture content in a drug product during manufacturing process when the drug products were prepared by the wet granulation process using aqueous solutions of general binders or by a heating and/or moisturizing process of the resulting composition after the production manufacturing process. The inventors found that a stable solid formulation of solifenacin or a salt thereof wherein the degradation thereof over time could be inhibited could be produced when the ratio of amorphous solifenacin in crystalline and amorphous solifenacin was at a given value or less.

Furthermore, the inventors found that a formulation of solifenacin wherein the degradation of solifenacin over time could be inhibited could be produced when polyethylene glycol (Macrogol under another name; abbreviated as PEG hereinafter) was used as a binder irrespective of the manufacturing process thereof, although PEG itself was a substance to be used generally for the purpose of preparing drugs into an amorphous state. Thus, the invention has been achieved, other than the stabilization process described above.

In other words, the invention relates to those described below.

1. A composition of solifenacin or a salt thereof for use in solid formulation, the composition containing the crystal of solifenacin or a salt thereof, wherein the amorphous content is within a range showing no influence on drug product stability.
2. A composition of solifenacin or a salt thereof for use in solid formulation, as described above in 1, wherein the amorphous content is 77% or less.
3. A composition for use in solid formulation, as described above in 1 or 2, which is produced by a manufacturing process including a step of blending solifenacin or a salt thereof with excipients without using a solvent, followed by compression-molding.
4. A composition for use in solid formulation, as described above in 1 or 2, which is produced by a manufacturing process including a step of adding a solvent to solifenacin or a salt thereof, wherein the amount of solifenacin or a salt thereof to be dissolved per 1 mL of the solvent is less than 0.1 mg.
5. A composition for use in solid formulation, as described above in 4, wherein the solvent added to solifenacin or a salt thereof is acetone or hexane or a mixture thereof.
6. A composition for use in solid formulation, as described above in 1 or 2, which is produced by a manufacturing process including a step of adding a solvent to prepare solifenacin or a salt thereof into an amorphous state, wherein the amount of solifenacin or a salt thereof to be dissolved per 1 mL of the solvent is 10 mg or more.
7. A composition for use in solid formulation, as described above in 6, wherein the solvent to prepare solifenacin or a salt thereof into an amorphous state is water, methanol or ethanol or a mixture thereof.
8. A composition for use in solid formulation as described above in 1 through 7, which is produced by a manufacturing process including a step of promoting the crystallization of amorphous solifenacin or an amorphous salt thereof.
9. A mixture of solifenacin or a salt thereof, wherein the mixture contains amorphous and crystalline solifenacin or an amorphous and crystal salt thereof and wherein the amorphous content of solifenacin or a salt thereof is within a range showing no influence on product stability.
10. A pharmaceutical composition for use in solid formulation, the composition containing crystalline and amorphous solifenacin or a crystalline and amorphous salt thereof, together with a inhibitor of amorphous preparation.
11. A pharmaceutical composition described above in 10, wherein the inhibitor of amorphous preparation is a substance showing ethylene oxide chain.
12. A pharmaceutical composition described above in 11, wherein the substance having ethylene oxide chain is polyethylene glycol.

When compressed according to a formulation in blend with an additive, techniques are known, including a stabilization technique of (E)-1-[4-(2-dimethylamino)ethoxy]phenyl-2-(4-isopropylphenyl)-1-(4-phosphonooxy)phenyl-1-butene with a property such that degradation products thereof increase in an accelerating manner over time under influences such as moisture contained in such additive, the increase in the contact of the tablet inside with the additive via pressure molding, and the reduction of the crystallinity via pressurization and with an efficacy as a therapeutic agent of breast cancer via moisture reduction (Chemical & Pharmaceutical Bulletin, 42(12), 2582(1994)), and a stabilization technique of a composition containing the compound by the melt granulation manufacturing process (JP-A-Hei 9-110698) for example a stabilization technique (JP-A-Hei 10-007547) by a substantially anhydrous process of manufacturing a solid formulation in a tablet form of anilide compounds for use in multiple sclerosis, which involves much difficulty in accurately administering the anilide compounds as the principal component because compounds different from the principal compound in the solid formulation are generated at 6 to 9% during storage.

However, these technical references never include any description of solifenacin or a salt thereof with a structure totally different from those of disclosed compounds and with physicochemical or pharmacological properties totally different from those of disclosed compounds or never include any description or suggestion about the problem of the degradation of a solid formulation containing amorphous form over time or about the stabilization thereof by adjusting the amorphous content below the appropriate amount in the resulting solid formulation.

The official gazette of JP-A-Hei-5-194218 discloses a stabilization technique of nitrogen-containing hetero-ring alkylphenyl derivatives with an anti-angiotensin II action, of which the content reduction is accelerated via crystalline deformation due to kneading during production course, and pressure, abrasion, heat and the like imposed during granulation or pressure molding, wherein the technique includes a step of blending an oily substance with a low melting point such as PEG in such alkylphenyl derivatives to stabilize the resulting oral formulation, when the alkylphenyl derivatives are formulated according to a formulation in blend with other components. In this case, the stabilization mechanism with the substance with a low melting point is via the inhibition of the thermal degradation of the active pharmaceutical ingredient by blending the oily substance with a low melting point uniformly in the active pharmaceutical ingredient. No description is included therein about the contribution of the substance with a low melting point to the crystallinity of the active pharmaceutical ingredient. The mechanism is totally different from the stabilization mechanism in accordance with the invention.

Additionally, International Journal of Pharmaceutics, 216 (2001) 43-49 reports that in co-dissolving and crystallizing lactose with PEG, the precipitated lactose exists in a crystal state. Alternatively, International Journal of Pharmaceutics, 127 (1996) 261-272 and International Journal of Pharmaceutics, 262(2003)125-137 report that in co-dissolving and crystallizing a drug with PEG, the drug is at an amorphous state. In case of co-dissolving and crystallizing an active pharmaceutical ingredient with polymer such as PEG, generally, the resulting active pharmaceutical ingredient is frequently in an amorphous state, although it depends on the properties of the active pharmaceutical ingredient. Research works about blending for the purpose of amorphous preparation via the solubilization of slightly soluble drugs and the like have been known commonly. All compounds disclosed in these technical references have chemical structures totally different from the structure of solifenacin. The references never include any description about solifenacin or a salt thereof with different physicochemical and pharmacological properties or any suggestion about a finding to establish the anticipation about the crystallization or amorphous preparation of solifenacin via the blending with PEG. Even about stabilization, the references never describe or suggest the constitution such that the degradation of the active pharmaceutical ingredient over time can be inhibited by utilizing the crystallization via polymers such as PEG.

The inventive composition is now described below in detail.

The "salt of solifenacin" for use in accordance with the invention includes acid addition salts of solifenacin with mineral acids such as hydrochloric acid, hydrobromic acid, hydroiodic acid, sulfuric acid, nitric acid, phosphoric acid, organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid and glutamic acid, and quaternary ammonium salts thereof, as described in the patent reference 1. Specifically, solifenacin succinate is preferable in providing a pharmaceutical product and also achieves the stabilization effect greatly in accordance with the invention. Thus, the succinate salt is particularly selected.

"Solifenacin or a salt thereof" for use in accordance with the invention is readily available by the processes described in the patent reference 1 or according to the processes or by routine methods. The quantity of solifenacin or a salt thereof to be blended in the composition for use in solid formulation in accordance with the invention satisfactorily contains an active quantity thereof per unit dose formulation. The quantity is preferably at 0.001% by weight to 97% by weight, more preferably at 0.05% by weight to 50% by weight, still more preferably at 0.05% by weight to 20% by weight, most preferably at 0.05% by weight to 10% by weight. When the pharmaceutical composition of the invention is a particle such as granule, the quantity of the drug blended in the particle pharmaceutical composition is appropriately selected, generally depending on the types of the drug or the pharmaceutical use (indication) thereof. A therapeutically active quantity thereof or a prophylactically active quantity thereof is satisfactory, with no specific limitation.

Additionally, the daily dose of solifenacin or a salt thereof is preferably 0.01 mg to 100 mg, more preferably 0.5 mg to 50 mg, still more preferably 0.5 mg to 20 mg, most preferably 0.5 mg to 10 mg.

The "crystal" or "crystalline substance" of solifenacin or a salt thereof means a substance of solifenacin or a salt thereof with the crystalline structure referred to in the crystallography field as the term means. In accordance with the invention, the crystal or crystalline means a substance with less solifenacin degradation over time. The term crystal or crystalline means a substance different from an amorphous substance with significant solifenacin degradation over time when the substance exists over the range with no influence on drug product stability in a formulation.

In accordance with the invention, meanwhile, the term "amorphous" solifenacin or a salt thereof or "amorphous substance" of solifenacin or a salt thereof mean a substance with a crystallographically amorphous structure. In accordance with the invention, meanwhile, the term "amorphous solifenacin or amorphous salt thereof" or "amorphous substance of solifenacin or a salt thereof" means a substance with a significant degradation of solifenacin when it exists over the range with no influence on drug product stability and additionally means a substance different from the "crystal" or the "crystalline substance" with less solifenacin degradation over time.

In accordance with the invention, additionally, the "amorphous content" means the ratio of the amorphous substance to the total of amorphous and crystalline solifenacin or an amorphous and crystal salt thereof.

In accordance with the invention, the phrase "within a range with no influence on drug product stability" means that the product of solifenacin or a salt thereof is stable under severe conditions during the distribution course of the commercial product. Specifically, the quantity of the main generated degradation product of solifenacin to the total of solifenacin or a salt thereof and degradation products thereof can be inhibited to 0.4% or less at a preliminary stability test using bottle-sealing conditions at 40° C. and 75% RH for 6 months.

In accordance with the invention, therefore, the specific amorphous content within a range with no influence on product stability is 77% or less, preferably 73% or less, still more preferably 71% or less, most preferably 63% or less to the total of amorphous and crystalline solifenacin or an amorphous and crystal salt thereof in case of measurement by near infrared spectrometry. Furthermore, solifenacin or a salt thereof with an initial amorphous content exceeding a range with no influence on product stability immediately after the production but progressing the crystallization over time so that the amorphous content falls within a range with no influence on product stability is also included within the scope of the invention. Thus, the timing for the measurement of the amorphous content is with no specific limitation. Taking into account that the amorphous content is to certify product stability during the distribution course, preferably, the amorphous content is measured at the time of the start of the distribution of the product or in an appropriate timing thereafter.

The method for assessing the amorphous content of solifenacin or a salt thereof in accordance with the invention is generally any method for identifying the crystalline structure of solifenacin or a salt thereof in the composition but includes for example powder X ray diffraction method, DSC method, solid NMR and near infrared spectrometry. For measuring the crystalline structure of a drug at a lower content in a mixture composition with other components, in particular, the crystalline structure is preferably measured by solid NMR or near infrared spectrometry. A method for measuring the structure in a simpler way is near infrared spectrometry.

As the method for measuring the amorphous content of solifenacin succinate, for example, a method by near infrared spectrometry was used by measuring the spectrum with a Fourier transform near infrared spectrometer (Vector 22/N, Bruker Optik GmbH, Germany) (a measurement range; 10000 $cm^{-1}$ to 4000 $cm^{-1}$, resolution; 2 $cm^{-1}$, scan number; 126) and secondary derivation of the resulting spectrum (Savitzky-Gollay convolution method) for analysis with a near infrared spectral analysis software (for example, OPUS, Bruker Optik GmbH, Germany). Prior to the spectral measurement of the tablet, the spectra of products prepared by mixing together various ratios of crystalline and amorphous solifenacin succinate preliminarily prepared by spray-drying method of aqueous solifenacin succinate solution are analyzed by regression analysis by the partial least squares method, to prepare a standard curve. Inserting the spectrum of the tablet on the standard curve, the amorphous content of solifenacin succinate can be determined.

As the method for measuring the amorphous content of solifenacin succinate by solid NMR, for example, the spectrum of the tablet is measured with a solid NMR apparatus (for example CMX-300, manufactured by Chemagnetics, USA) (for example, probe used; made of ceramics, 7.5 mm probe, contact time; 9 msec, pulse repeat time; 38 sec, sample rotation number; 5 kHz). The resulting spectrum is data-processed (for example, index function window, broadening factor; 30 Hz, trapezoid window; t1=0, t2=0, t3=0.5, t4=0.6). Furthermore, crystalline and amorphous solifenacin succinate preliminarily prepared by spray-drying method of aqueous solifenacin succinate solution are mixed together at various ratios. Using then lactose as an internal standard, the peak/height ratio of crystalline solifenacin succinate is determined to prepare a standard curve. Inserting the peak/height ratio of crystalline solifenacin succinate resulting from the tablet spectrum on the standard curve, the crystal content of solifenacin succinate and the amorphous content can be determined.

The "composition for use in solid formulation" in accordance with the invention is any pharmaceutical composition for use in solid formulation with no specific limitation, wherein the degradation of solifenacin or a salt thereof over time can be inhibited because the amorphous content is within a range with no effect on product stability. The term means oral and parenteral compositions such as tablets, pills, powders, granules and capsules.

The phrase "mixture of solifenacin or a salt thereof containing amorphous and crystalline solifenacin or an amorphous and crystalline salt thereof, wherein the amorphous content is within a range with no influence on product stability" means a mixture of amorphous and crystalline solifenacin or an amorphous and crystalline salt thereof, wherein the degradation of solifenacin or a salt thereof is inhibited over time and the mixture essentially contains amorphous solifenacin or an amorphous salt thereof with an amorphous content within a range with no influence on product stability.

As to the amount of solifenacin or a salt thereof to be blended in the composition for use in solid formulation in accordance with the invention, the composition satisfactorily contains an active amount of solifenacin or a salt thereof per unit dose formulation.

The method for producing the "composition of solifenacin or a salt thereof for use in solid formulation, the composition containing crystalline solifenacin or a crystalline salt thereof, wherein the amorphous content of solifenacin or a salt thereof is within a range with no influence on product stability" is any of a method with no use of any solvent to prepare solifenacin or a salt thereof into an amorphous state, or a method including a step of reducing the contact of solifenacin or a salt thereof with a solvent in the course of dissolving solifenacin or a salt thereof in the solvent to prepare solifenacin or a salt thereof into an amorphous state to generate the amorphous substance, wherein the amorphous content is within a range with no influence on product stability, or a method including a step of heating and/or moisturizing a composition with an amorphous content over the range with no influence on product stability during the production or after the production, to adjust the amorphous content within a range with no influence on product stability, with no specific limitation to either the apparatus or the means.

As the production conditions to adjust the amorphous content of solifenacin or a salt thereof within a range with no influence on product stability, various production conditions can be suggested. Specifically, one of the production conditions is characteristically a production process with no use of any solvent to prepare solifenacin or a salt thereof into an amorphous state. For the phrase "production process with no use of any solvent to prepare solifenacin or a salt thereof into an amorphous state", a production process by direct tableting is included, which comprises mixing solifenacin or a salt thereof with an appropriate excipients with no use of any solvent and compress molding the resulting mixture if necessary to obtain a tablet. In case that the method includes a step of adding a solvent, the method includes using a solvent hardly preparing solifenacin or a salt thereof into an amorphous state, wherein the amount of solifenacin or a salt thereof to be dissolved in 1 mL of the solvent is less than 0.1 mg, for example acetone, hexane or a mixture thereof, for wet granulation.

In case of a manufacturing process to prepare solifenacin or a salt thereof into an amorphous state, in a manufacturing step of adding a solvent preparing solifenacin or a salt thereof into an amorphous state, a stable composition of solifenacin or a salt thereof for use in solid formulation can be produced under manufacturing conditions for reducing the amount and addition rate of solvents added, such as water to be used in the manufacturing step and under production conditions for securely achieving the intended quality of the resulting granule, to adjust the amorphous content within a range with no influence on product stability. The solvent to prepare solifenacin or a salt thereof into an amorphous state as referred to herein means a solvent wherein the amount of solifenacin or a salt thereof to be dissolved in 1 mL of the solvent is 10 mg or more, for example, water, methanol or ethanol or mixtures thereof, which is more preferably water. Specifically, in a step of spraying an aqueous solution dissolved therein as a binder solution on a powder containing solifenacin or a salt thereof in producing the composition for use in solid formulation, the product is satisfactorily manufactured by preparing a granule with a moisture content adjusted to a given value or less during the spraying of the binder solution. The moisture content in the granule during or after the spraying of a binder solution is adjusted to preferably 9% or less, more preferably 6% or less, particularly preferably 5% or less, most preferably 4% or less.

Even when a composition at an amorphous content of solifenacin or a salt thereof being 77% or more is produced not by the manufacturing method described above but by the general wet granulation method, the crystallization process of the composition is promoted to obtain a composition at an amorphous content of solifenacin or a salt thereof within a range with no influence on product stability. The promotion of the crystallization process as referred to herein may be done by any manufacturing process of promoting the crystallization of amorphous solifenacin or a salt thereof, with no specific limitation. The manufacturing process includes for example heating and/or moisturizing process, microwave irradiation process, low-frequency irradiation process, ultrasonic irradiation process, and thermoelectron irradiation process. The heating and/or moisturizing process includes a manufacturing process of leaving the substance to stand alone in a thermostat at a constant humidity, for example under conditions of 25° C. and 75% RH for one week for subsequent re-drying. Any manufacturing process of heating and/or moisturizing the composition uniformly may be satisfactory, with no specific limitation to the apparatus and the means. For the microwave irradiation process, for example a wavelength of 10 MHz to 25 GHz may be used. Additionally, the processing time depends on the initial crystallization degree and the selected substrate. The wavelength described above is used for irradiation for example for 10 seconds to 60 minutes. Irradiation may be done continuously or intermittently. The timing for these crystallization-promoting processes may be any timing when a stable composition of solifenacin or a salt thereof for use in solid formulation can be obtained, with no specific limitation. Manufacturing a granule of solifenacin or a salt thereof or after producing a composition for use in solid formulation.

The manufacturing process includes for example a direct tableting process of mixing solifenacin or a salt thereof with an appropriate additive and compress molding the mixture if necessary to obtain a tablet, a wet granulation process of mixing solifenacin or a salt thereof with an appropriate additive and then spraying a binder solution on the resulting mixture to prepare a granule, and a melt granulation process of mixing solifenacin or a salt thereof with an appropriate substance with a low melting point and heating and granulating the mixture. Since solifenacin or a salt thereof has strong aggregation property so it is difficult to securely keep the content uniformity and the mixture sticks to punches during compression by the direct tableting process, and it is very difficult to control the amount of a substance with a low melting point to be dissolved by the melt granulation process, the wet granulation process is preferable as the manufacturing process in accordance with the invention.

The wet granulation process includes for example a process of pulverizing solifenacin or a salt thereof with a pulverizing machine, subsequently mixing the resulting powder with a pharmaceutically acceptable additive such as excipients and disintegrators, spraying a binder solution on the mixture to prepare a granule, mixing a lubricant into the granule, and compressing the mixtures into a tablet. According to the process, it is understood that crystalline solifenacin or a crystal salt thereof is dissolved in the sprayed binder solution at the step of spraying the binder solution for granulation and then drying the resulting granule, to generate the amorphous product. By reducing the spray rate of the binder solution during granulation, reducing the total amount of the binder solution, or raising the temperature of charged air or the like to reduce the dissolution of solifenacin or a salt thereof in the binder solution to consequently reduce the generated amorphous form, a pharmaceutical composition for use in solid formulation can be supplied.

The preferable spray rate of a binder solution, depending on the manufacturing process or the manufacturing scale. The spray rate is preferably 40 to 100 g/min, more preferably 50 to 80 g/min when manufactured at a 5-kg scale by a fluidized bed granulation process. The preferable total amount of a binder solution, depending on the manufacturing process or the manufacturing scale. For production at a 5-kg scale by the fluidized bed process, the total amount thereof is preferably 1000 kg to 2500 kg, more preferably 1500 kg to 2200 kg. The preferable charged air temperature varies depending on the production process or the production scale. For production at a 5-kg scale by the fluidized bed process, however, the temperature is preferably 50 to 80° C., more preferably 60 to 80° C.

The pulverizing machine includes for example hammer mill, ball mill, jet mill and colloid mill. Generally, any process capable of pharmaceutical pulverization may be satisfactory, with no specific limitation to the apparatus or the means.

The blending apparatus of the individual components as used continuously to pulverization includes for example Type V mixer, ribbon-type mixer, container mixer, and high-speed agitation. Generally, any process capable of pharmaceutically uniformly mixing the individual components may be satisfactory, with no specific limitation to the apparatus or the means.

The granulation apparatus (process) includes for example high-speed agitation granulation process, fluidized bed granulation process, extrusion granulation process, and rolling granulation process. Any granulation process using a binder solution may be satisfactory, with no specific limitation to the apparatus or the means.

The tableting apparatus includes for example rotary tableting machine and single tableting machine. Generally, any process capable of producing compress-molded products (preferably, tablets) may be satisfactory, with no specific limitation to the apparatus or the means.

The binder for use in the wet granulation process includes for example hydroxypropylmethyl cellulose, and polyvinylpyrrolidone. Generally, any binder with a pharmaceutically acceptable powder-binding power may be satisfactory, with no specific limitation.

Generally, the amount of such binder to be used may be an amount thereof to give a pharmaceutically acceptable granulation product, with no specific limitation. Generally, the amount is 0.5 to 50% by weight per unit dose, preferably 0.5 to 10% by weight per unit dose, more preferably 2 to 5% by weight per unit dose.

For such pharmaceutical composition for use in solid formulation in accordance with the invention, further, various pharmaceutical excipients may appropriately be used for formulation. Such pharmaceutical excipients may be any pharmaceutically acceptable and pharmacologically acceptable excipients, with no specific limitation. For example, binders, disintegrators, sour agents, foaming agents, artificial sweeteners, flavor, lubricants, coloring agents, stabilizers, buffers, anti-oxidants, and surfactants may be used. For example, the binders include hydroxypropylmethyl cellulose and gum Arabic. The disintegrating agents include for example corn starch, potato starch, calcium carmellose, and sodium carmellose. The sour agents include for example citric acid, tartaric acid and malic acid. The foaming agents include for example sodium bicarbonate. The artificial sweeteners include for example saccharine sodium, glycyrrhizin dipotassium, aspartame, stevia, and somatin. The flavor includes for example lemon, lemon lime, orange and menthol. The lubricants include for example magnesium stearate, calcium stearate, sucrose fatty acid ester, polyethylene glycol, talc, and stearic acid. The coloring agents include for example yellow iron sesquioxide, red iron sesquioxide, Edible Yellow Nos. 4 and 5, Edible Red Nos. 3 and 102, and Edible Blue No. 3. The buffers include for example citric acid, succinic acid, fumaric acid, tartaric acid, ascorbic acid or salts thereof, glutamic acid, glutamine, glycine, aspartic acid, alanine, arginine or salts thereof, magnesium oxide, zinc oxide, magnesium hydroxide, phosphoric acid, boric acid or salts thereof. The anti-oxidants include for example ascorbic acid, dibutylhydroxytoluene, propyl gallate. The surfactants include fore example polysorbate 80, sodium laurylsulfate, and polyoxyethylene hardened castor oil. One type or two types or more of such excipients may appropriately be added in combination at an appropriate amount.

Further, the "inhibitor of amorphous preparation" means a substance inhibiting the generation of amorphous solifenacin or an amorphous salt thereof when solifenacin or a salt thereof is dissolved in a solvent and then solidified by drying and the like in preparing a composition of solifenacin or a salt thereof for use in solid formulation, using a solvent.

The inhibitor of amorphous preparation is preferably a substance with ethylene oxide chain. The substance with ethylene oxide chain as herein referred to is any substance with ethylene oxide chain with no specific limitation. As long as the purpose of inhibiting the amorphous preparation of solifenacin or a salt thereof in accordance with the invention is achieved by adding a substance, the substance may be any molecular species or have any molecular weight or any polymerization degree, with no specific limitation. The molecular weight is preferably within an average molecular range of 400 to 1,000,000, more preferably within an average molecular range of 2,000 to 200,000. As the substance with ethylene oxide chain, two or more types of the substance may be used in mixture. In accordance with the invention, specifically, the substance with ethylene oxide chain includes for example PEG, polyethylene oxide, polyoxyethylene polyoxypropylene block copolymer, polyoxyethylene hardened castor oil (abbreviated as HCO hereinafter), and polyethylene glycol fatty acid ester. Among them, in particular, PEG, polyoxyethylene polyoxypropylene block copolymer or HCO is preferable. PEG is more preferable.

The polyoxyethylene polyoxypropylene block copolymer in accordance with the invention may be a copolymer of propylene oxide and ethylene oxide. Depending on the composition ratio, various such copolymers exist. Any such copolymer with a composition ratio with a property to inhibit amorphous preparation of solifenacin or a salt thereof may be satisfactory. Specifically, for example, polyoxyethylene (105) polyoxypropylene (5) glycol and polyoxyethylene (160) polyoxypropylene (30) glycol (Pluronic F68 under another name) may be used.

The inhibitor of amorphous preparation is used at an amount of preferably 0.1 to 90% by weight, more preferably 1 to 60% by weight to the total of the formulation. When PEG is used as a binder for use in the wet granulation process by dissolving PEG in distilled water, the amount is preferably 3 to 20% by weight, more preferably 4 to 10% by weight to the powder to be granulated. When the amount of the inhibitor of amorphous preparation is examined relatively to one part by weight of crystalline and amorphous solifenacin or salt thereof, the amount is preferably at a ratio of 0.001 to 100,000% by weight, more preferably at a ratio of 1 to 1,000% by weight, still more preferably at a ratio of 10 to 600% by weight.

In accordance with the invention, the phrase "containing" means that solifenacin or a salt thereof as the active pharmaceutical ingredient is in mixture with the inhibitor of amorphous preparation. Preferably, solifenacin or a salt thereof is in contact with an inhibitor of amorphous preparation so that solifenacin or a salt thereof is distributed in a state of mixture. As in the case of using a pharmaceutical composition as a coating agent of solifenacin formulation wherein the active pharmaceutical ingredient, solifenacin or a salt thereof, is not in contact with or in mixture with such inhibitor of amorphous preparation so that it exists in a localized state (for example the inhibitor of amorphous preparation in accordance with the invention (PEG)), pharmaceutical preparations for example at a state such that solifenacin or a salt thereof is not in physical contact with a inhibitor of amorphous preparation in an intermediate layer using other additives and the like are excluded.

A pharmaceutical composition of solifenacin or a salt thereof for use in solid formulation in accordance with the invention is now described in detail. In the following Examples and Comparative Examples, the invention is described in more detail. However, the invention is not construed in a limited manner by them.

REFERENCE EXAMPLE 1

60 parts of solifenacin succinate were dissolved in 140 parts of water, for spray-drying with a spray dryer (DL-41, manufactured by Yamato Science), to obtain a spray-dried product.

The crystallinity of the resulting spray-dried product of solifenacin succinate was measured by an X-ray diffraction apparatus (RINT 1400 manufactured by Rigaku Denki). A halo pattern was observed, indicating the product was amorphous.

<Storage Stability of Crystalline and Amorphous Product>

The results of the stability of the crystalline product, before spray-drying, and amorphous product are shown in Table 1. The amounts of degradation products over time under storage were measured by high-performance liquid chromatography. The maximum amount of the individual degradation products is shown. In a short period of time after the start of storage, degradation products of amorphous solifenacin succinate product were generated and the stability thereof was poorer than that of the crystalline product. Therefore, the main cause of the degradation of the active pharmaceutical ingredient over time was presumably amorphous solifenacin succinate generated in the manufacturing process of the formulation.

Results of the stability of crystalline product and amorphous product of solifenacin succinate
Storage conditions: 40° C. and 75% RH
Packaging form: glass vial
Test items: related substances (individual maximum values)

TABLE 1

| Storage conditions | | Crystalline product | Amorphous product |
| --- | --- | --- | --- |
| Initial | | ND | ND |
| Sealed glass vial | one-week later | ND | 0.03% |
| | two-week later | ND | 0.05% |
| Open glass vial | one-week later | ND | 0.16% |
| | two-week later | ND | 0.16% |

ND: not detectable

EXAMPLE 1

204 parts of hydroxypropylmethyl cellulose 2910 was dissolved and agitated in 1836 parts of water with an air motor agitator (AM-GC-1, manufactured by Chuo-Rika Machine), to prepare a binder solution (at a concentration of 10.0 W/V %). Then, 340 parts of solifenacin succinate and 1360 parts of lactose were mixed together. Then, the resulting mixture was pulverized with a hammer mill (sample mill AP-S using 1-mm screen, manufactured by Hosokawa Micron). 2125 parts of lactose and 1020 parts of corn starch were added to the mixed and pulverized product and then were charged in a fluidized bed granulation machine (WSG-5 manufactured by Powlec) for spraying the binder solution at a charged air temperature of 65° C., an air flow volume of 4 m$^3$/min, a spray rate of the binder solution at 75 g/min, a spraying air pressure of 1.5 kg/cm$^2$, and a spray/shaking cycle of 30 seconds/10 seconds, for granulation. The moisture content in the granule when sprayed with the total volume of the binder solution was 3.9%. After granulation, the granule was dried at a charged air temperature of 50° C. for 10 minutes, to obtain the granule of the invention. 12 parts of magnesium stearate were added to 1188 parts of the dried granulated product for mixing with a mixer (type DC manufactured by Yamanouchi). Thereafter, the resulting mixture was compressed with a rotary tableting machine (HT P-22 manufactured by Hata Tekkosho) with a 7.5 mm-φ punch at a tableting pressure at about 700 kgf/punch to a tablet weight of 150 mg. Further, 800 parts of the resulting tablet were sprayed and coated with a solution prepared by dissolving/dispersing 84.3 parts of hydroxypropylmethyl cellulose, 15.8 parts of Macrogol 6000, 25.3 parts of talc, 10.5 parts of titanium oxide, and 0.03 part of red iron sesquioxide in 1223 parts, using an aerated coating machine (high coater HCT-30 manufactured by Freund Industry Corporation) at a charged air temperature of 60° C., a pan rotation velocity of 13 rpm, and a coating fluid feed rate of 5 g/min to a 2.7-% ratio of the coating agent to the tablet weight, to obtain the film-coated tablet of the invention.

EXAMPLE 2

Granulation was done by spraying the binder solution under granulation conditions with a fluidized bed granulation machine such that the charged air temperature was 65° C.; the air flow volume was 4 m$^3$/min; the binder solution spray rate was 75 g/min; the spray air pressure was 0.7 kg/cm$^2$; and the cycle of spray/shaking was 30 seconds/10 seconds. The moisture content in the granule was 5.5% when the total volume of the binder solution was sprayed. After granulation, the film-coated tablet of the invention was prepared by the method described in Example 1.

EXAMPLE 3

Granulation was done by spraying the binder solution under granulation conditions with a fluidized bed granulation machine such that the charged air temperature was 65° C.; the air flow volume was 4 m$^3$/min; the binder solution spray rate was 95 g/min; the spray air pressure was 1.5 kg/cm$^2$; and the cycle of spray/shaking was 30 seconds/10 seconds. The moisture content in the granule was 5.7% when the total volume of the binder solution was sprayed. After granulation, the film-coated tablet of the invention was prepared by the method described in Example 1.

EXAMPLE 4

Granulation was done by spraying the binder solution under granulation conditions with a fluidized bed granulation machine such that the charged air temperature was 55° C.; the air flow volume was 4 m$^3$/min; the binder solution spray rate was 75 g/min; the spray air pressure was 1.5 kg/cm$^2$; and the cycle of spray/shaking was 30 seconds/10 seconds. The moisture content in the granule was 8.4% when the total volume of the binder solution was sprayed. After granulation, the film-coated tablet of the invention was prepared by the method described in Example 1.

COMPARATIVE EXAMPLE 1

Granulation was done by spraying the binder solution under granulation conditions with a fluidized bed granulation machine such that the charged air temperature was 65° C.; the air flow volume was 4 m$^3$/min; the binder solution spray rate was 115 g/min; the spray air pressure was 1.5 kg/cm$^2$; and the cycle of spray/shaking was 30 seconds/10 seconds. The moisture content in the granule was 10.6% when the total volume of the binder solution was sprayed. After granulation, the film-coated tablet of the invention was prepared by the method described in Example 1.

COMPARATIVE EXAMPLE 2

Granulation was done by spraying the binder solution under granulation conditions with a fluidized bed granulation machine such that the charged air temperature was 65° C.; the air flow volume was 3 m$^3$/min; the binder solution spray rate was 75 g/min; the spray air pressure was 1.5 kg/cm$^2$; and the cycle of spray/shaking was 30 seconds/10 seconds. The moisture content in the granule was 10.6% when the total volume of the binder solution was sprayed. After granulation, the film-coated tablet of the invention was prepared by the method described in Example 1.

COMPARATIVE EXAMPLE 3

Granulation was done by spraying the binder solution under granulation conditions with a fluidized bed granulation machine such that the charged air temperature was 45° C.; the air flow volume was 4 m$^3$/min; the binder solution spray rate was 75 g/min; the spray air pressure was 1.5 kg/cm$^2$; and the cycle of spray/shaking was 30 seconds/10 seconds. The moisture content in the granule was 10.8% when the total volume of the binder solution was sprayed. After granulation, the film-coated tablet of the invention was prepared by the method described in Example 1.

<Measuring the Moisture Content of Granule During Granulation, the Content of Amorphous Solifenacin Succinate in the Tablet and the Amount of Degradation Products After Storage Over Time>

The results of the moisture content of granule after spraying the binder solution, the content of amorphous solifenacin succinate and the preliminary stability using bottle-sealing conditions at 40° C. in 75% RH for 6 months are shown in Table 2 when manufacturing conditions were modified during granulation. The moisture content of granule after spraying the binder solution is shown as the value measured by loss on drying method (80° C., 2 hours), while the content of amorphous solifenacin succinate is shown as the value measured by near infrared spectrometry. The near infrared spectrometry was done by measuring the spectrum by Fourier Transform near infrared spectrometer (Vector 22/N, Bruker Optik GmbH, Germany) (measured range of 10000 cm$^{-1}$ to 4000 cm$^{-1}$, resolution; 2 cm$^{-1}$, scan number; 126). The resulting spectrum was secondarily derivative (Savitzky-Gollay convolution method) and analyzed with a near infrared spectrum analysis software (OPUS, Bruker Optik GmbH, Germany). Before measuring the spectrum of the tablet, the spectra of products prepared by mixing crystalline and amorphous solifenacin succinate preliminarily prepared by spray-drying an aqueous solifenacin succinate solution at various ratios were subjected to regression analysis by partial least squares method to prepare a standard curve. The spectrum of the tablet was inserted on the standard curve to determine the amount of amorphous solifenacin succinate. Additionally, the amounts of degradation products after storage for 6 months using bottle-sealing conditions at 40° C. in 75% RH were measured by high-performance liquid chromatography. Among the amounts of degradation products as thus determined, the amount of the main degradation product (F1) generated to the total amount of solifenacin succinate and degradation products thereof is shown. Using the ratio of the generated F1 as an indicator, the stability of solifenacin succinate was examined.

Moisture content of granule during granulation in 10-mg tablet of solifenacin succinate, the content of amorphous solifenacin succinate in the tablet and the preliminary test of the stability (for 6 months)

TABLE 2

| Test items | Example 1 | Example 2 | Example 3 | Example 4 | Comparative Example 1 | Comparative Example 2 | Comparative Example 3 |
|---|---|---|---|---|---|---|---|
| Moisture content of granule after spraying | 3.9% | 5.5% | 5.7% | 8.4% | 10.6% | 10.6% | 10.8% |
| Content of amorphous solifenacin succinate in the tablet (at the time of start of storage) *1 | 63% | 73% | 71% | 77% | 92% | 90% | 92% |
| Ratio of generated F1 *2 | 0.31% | 0.29% | 0.35% | 0.38% | 0.48% | 0.44% | 0.43% |

*1: measured by near infrared spectrometry
*2: ratio of principal degradation product of solifenacin succinate to the total amount of solifenacin succinate and degradation products thereof As shown in Table 2, the 10-mg tablets prepared under the individual manufacturing conditions have different moisture contents during granulations. As the moisture contents in the granules were lower, generally, the amorphous contents in the tablets were lower.

In Comparative Examples 1 through 3 as general manufacturing processes, the moisture contents in the granules after spraying binder solutions were larger than in the Examples. Therefore, the amorphous solifenacin contents were as large as 90% or more. Additionally, the amount of the main degradation product F1 to the total of solifenacin succinate and degradation products thereof exceeds 0.4%. This indicates that a serious problem exists in providing a composition of solifenacin or a salt thereof being stable over time to clinical practice.

In case of controlling the moisture content in the granule as less as possible as in Examples 1 through 4, alternatively, the amorphous contents under controls of moisture content were 77% or less, while the amount of the main degradation product F1 to the total of solifenacin succinate and degradation products thereof was 0.4% or less.

Thus, a solifenacin formulation stable over time can be provided by controlling the amorphous content to 77% or less in a formulation containing solifenacin or a salt thereof.

EXAMPLE 5

270 parts of PEG (Macrogol 6000 under trade name, manufactured by Sanyo Chemical) were dissolved and agitated in 1080 parts of water with an air motor agitator (AM-GC-1, manufactured by Chuo Rika) to prepare a binder solution (at a concentration of 20.0 W/V %). Then, 90 parts of solifenacin succinate and 360 parts of lactose (Lactose 200M under trade name, manufactured by DMV) were mixed together. Then, the resulting mixture was pulverized with a hammer mill (sample mill AP-S, using 1-mm screen, manufactured by Hosokawa Micron) 3906 parts of lactose and crystalline cellulose (Avicel PH 102 under trade name, manufactured by Asahi Chemical) were added to the mixed and pulverized product and then were charged in a fluidized bed granulation machine (WSG-5 manufactured by Powlec) for spraying the binder solution at a charged air temperature of 70° C., a spray rate of the binder solution at 100 g/min, a spraying air pressure of 1.5 kg/cm$^2$, and a spray/shaking cycle of 30 seconds/ 10 seconds, for granulation. After granulation, the granule was dried at a charged air temperature of 70° C. for 10 minutes, to obtain the granule of the invention. 12 parts of magnesium stearate (manufactured by NOF) were added to 1188 parts of the dried granulated product for blending with a mixer (type DC manufactured by Yamanouchi). Thereafter, the resulting mixture was compressed with a rotary tableting machine (HT P-22 manufactured by Hata Tekkosho) with a 5.5 mm-φ punch at a compression pressure of about 500 kgf/punch to a tablet weight of 60 mg. Further, 900 parts of the resulting tablet were sprayed and coated with a solution prepared by dissolving/dispersing 18.6 parts of HPMC 2910 (TC-5R under trade name, manufactured by Shin-estu Chemical), 3.5 parts of PEG (Macrogol 6000 under trade name, manufactured by Sanyo Chemical), 5.6 parts of talc (manufactured by Kihara Chemical), 2.3 parts of titanium oxide (manufactured by Freund Industry Corporation), and 0.05 part of red iron sesquioxide in 270 parts of water, using an aerated coating machine (high coater HCT-30 manufactured by Freund Industry Corporation) at a charged air temperature of 60° C., a pan rotation velocity of 13 rpm, and coating fluid feed rate of 5 g/min to a 3.3-% ratio of the coating component to the tablet weight, to obtain the film-coated tablet of the invention.

COMPARATIVE EXAMPLE 4

180 parts of HPMC 2910 (TC-5R under trade name, manufactured by Shin-estu chemical) were dissolved and agitated in 1620 parts of water with an air motor agitator (AM-GC-1, manufactured by Chuo Rika) to prepare a binder solution (at a concentration of 10.0 W/V %). Then, 75 parts of solifenacin succinate and 300 parts of lactose were mixed together. Then, the resulting mixture was pulverized with a hammer mill (sample mill AP-S, using 1-mm screen, manufactured by Hosokawa Micron). 2700 parts of lactose and 900 parts of corn starch (manufactured by Nihon Shokuhin) were added to the mixed and pulverized product and then were charged in a fluidized bed granulation machine (WSG-5 manufactured by Powlec) for spraying the binder solution at a charged air temperature of 60° C., a spray rate of the binder solution at 75 g/min, a spraying air pressure of 1.5 kg/cm², and a spray/shaking cycle of 30 seconds/10 seconds, for granulation. After granulation, the granule was dried at a charged air temperature of 60° C. for 10 minutes, to obtain the granule of the invention. 12 parts of magnesium stearate (manufactured by NOF) were added to 1188 parts of the dried granule for blending with a mixer (type DC manufactured by Yamanouchi). Thereafter, the resulting mixture was compressed with a rotary tableting machine (HT P-22 manufactured by Hata Tekkosho) with a 5.5 mm-φ punch at a compression pressure of about 500 kgf/punch to a tablet weight of 60 mg. Further, 900 parts of the resulting tablet were coated by the process shown in Example 5, to obtain the film-coated tablet of the invention.

COMPARATIVE EXAMPLE 5

108 parts of corn starch (manufactured by Nihon Shokuhin) were added to 2592 parts of water and then dissolved therein under heating to 80° C. Then, the resulting solution was cooled to ambient temperature, to prepare a binder solution. Then, 90 parts of solifenacin succinate and 360 parts of lactose were mixed together. Then, the resulting mixture was pulverized with a hammer mill (sample mill AP-S, using 1-mm screen, manufactured by Hosokawa Micron). 3708 parts of lactose and 1080 parts of corn starch were added to the mixed and pulverized product and then were charged in a fluidized bed granulation machine (WSG-5 manufactured by Powlec) for spraying the binder solution at a charged air temperature of 70° C., a spray rate of the binder solution at 90 g/min, a spraying air pressure of 1.5 kg/cm², and a spray/shaking cycle of 30 seconds/10 seconds, for granulation. After granulation, the granule was dried at a charged air temperature of 70° C. for 10 minutes, to obtain the granule of the invention. 13 parts of magnesium stearate were added to 129 parts of the dried granulated product for blending with a mixer (type DC manufactured by Yamanouchi). Thereafter, the resulting mixture was compressed with a rotary tableting machine (HT P-22 manufactured by Hata Tekkosho) with a 5.5 mm-φ punch at a compression pressure of about 500 kgf/punch to a tablet weight of 60 mg. Further, 800 parts of the resulting tablet were sprayed and coated by the process shown in Example 5, to obtain the film-coated tablet of the invention.

<Results of Preliminary Test of Stability of Formulation of Solifenacin as Prepared by Wet Granulation Process>

A preliminary stability test of a solifenacin succinate tablet manufactured with a binder solution different from those used in the granulation was done (under conditions of 25° C. and 60% RH). The results are shown in Table 3.

The table of Comparative Example 4 as produced using HPMC could not be stabilized sufficiently. Even when other binder types were examined, starch could not improve the stability as shown in Comparative Example 5. As shown in Example 5, meanwhile, the use of PEG could improve the stability. It was indicated that even under severer conditions of temperature and humidity than the conditions of 25° C. and 60% RH, the stability of solifenacin formulation could be retained.

Results of Preliminary Stability Test of Solifenacin Succinate Tablet
Storage conditions: 25° C. and 60% RH
Packaging form: packed in metal-capped HDPE bottle
Test items: related substances (amount of main degradation product F1 generated)

TABLE 3

|  | Example 5 | Comparative Example 4 | Comparative Example 5 |
| --- | --- | --- | --- |
| Initial | 0.07% | 0.10% | 0.07% |
| 3-month later | 0.11% | 0.12% | 0.17% |
| 6-month later | 0.11% | 0.34% | 0.35% |
| 12-month later | 0.17% | — | — |

HDPE: High density polyethylene

INDUSTRIAL APPLICABILITY

The technical feature of the invention resides in the elucidation of the cause of the degradation of the active pharmaceutical ingredient in a formulation containing solifenacin or a salt thereof over time, which was amorphous solifenacin or an amorphous salt thereof. By preparing such formulation by adjusting the amorphous content therein to a given value or less, a stable solid formulation of solifenacin or a salt thereof could first be provided, which was an industrially great advantage. In a formulation containing solifenacin or a salt thereof, additionally, an inhibitor of amorphous preparation was contained therein, to enable the provision of a stable pharmaceutical composition for use in solid, which was an industrially great advantage.

Thus, the invention is useful as a technique enabling the provision of a stable composition of solifenacin or a salt thereof for use in solid formulation, of which the development as a pharmaceutical product for pollakiuria and incontinence of urine has been strongly desired.

The invention claimed is:

1. A pharmaceutical composition of solifenacin or a salt thereof for use in a solid formulation, the composition containing crystalline and amorphous solifenacin or a crystalline and amorphous salt thereof, together with an inhibitor of an amorphous preparation, wherein the inhibitor of an amorphous preparation is a substance having an ethylene oxide chain and wherein a composition wherein the crystalline and amorphous solifenacin or a crystalline and amorphous salt thereof is not in contact with or in mixture with the inhibitor of an amorphous preparation is excluded.

2. The pharmaceutical composition according to claim 1, wherein the substance having an ethylene oxide chain is polyethylene glycol, polyethylene oxide, polyoxyethylene polyoxypropylene block copolymer, polyoxyethylene hardened castor oil, or polyethylene glycol fatty acid ester.

3. A pharmaceutical composition according to claim 2, wherein the substance having an ethylene oxide chain is polyethylene glycol.

* * * * *